US012576022B2

(12) United States Patent (10) Patent No.: US 12,576,022 B2
An et al. (45) Date of Patent: Mar. 17, 2026

(54) COSMETIC COMPOSITION COMPRISING FERMENTED GRAPE EXTRACT

(71) Applicants: Korea Institute of Dermatological Sciences Inc, Seoul (KR); COSTORY CO., LTD, Wonju-si (KR)

(72) Inventors: In Sook An, Seoul (KR); Ka Ram Kim, Seoul (KR); Ye Eun Joo, Namyangju-si (KR); Sang Jae Son, Changwon-si (KR); Shang Hun Shin, Seoul (KR); Han Kyun Kim, Seoul (KR)

(73) Assignee: Korea Institute of Dermatological Sciences Inc & COSTORY CO., LTD (KR)

( * ) Notice: Subject to any disclaimer, the term of this patent is extended or adjusted under 35 U.S.C. 154(b) by 333 days.

(21) Appl. No.: 18/269,362

(22) PCT Filed: Sep. 24, 2021

(86) PCT No.: PCT/KR2021/012990
§ 371 (c)(1),
(2) Date: Jun. 23, 2023

(87) PCT Pub. No.: WO2022/139125
PCT Pub. Date: Jun. 30, 2022

(65) Prior Publication Data
US 2024/0058260 A1 Feb. 22, 2024

(30) Foreign Application Priority Data

Dec. 23, 2020 (KR) ........................ 10-2020-0181488

(51) Int. Cl.
| A61K 36/00 | (2006.01) |
| A61K 8/9789 | (2017.01) |
| A61Q 19/08 | (2006.01) |

(52) U.S. Cl.
CPC ............ *A61K 8/9789* (2017.08); *A61Q 19/08* (2013.01); *A61K 2800/85* (2013.01)

(58) Field of Classification Search
CPC .................................................. A61K 2800/85
See application file for complete search history.

(56) References Cited

FOREIGN PATENT DOCUMENTS

| CN | 104263573 | A | * | 1/2015 |
| JP | 2016113386 | A | | 6/2016 |
| JP | 5970672 | B2 | | 8/2016 |
| KR | 1020130085012 | A | | 7/2013 |
| KR | 101456052 | B1 | | 11/2014 |
| KR | 20160039762 | A | * | 4/2016 | ............ A61Q 19/08 |
| KR | 1020170049756 | A | | 5/2017 |
| KR | 101778538 | B1 | | 9/2017 |
| KR | 1020200071334 | A | | 6/2020 |
| WO | 2022139125 | A1 | | 6/2022 |

OTHER PUBLICATIONS

International Search Report & Written Opinion; PCT Application No. PCT/KR2021/012990; mailed Dec. 28, 2021.
Lee, In-Ae et al., "Improvement of Antioxidant Activity of Grape Skin by Alcohol Fermentation", Cancer Prevention Research. 2009, vol. 14, No. 1, pp. 77-83.
Park, Tae-Soon et al., "A Study on Biological Activities of Fermented Jujube and Grape", Microbiology and Biotechnology Letters. 2014, vol. 42, No. 2, pp. 106-113.

* cited by examiner

*Primary Examiner* — Qiuwen Mi
(74) *Attorney, Agent, or Firm* — NOVAK DRUCE CARROLL LLP

(57) ABSTRACT

According to an exemplary embodiment of the present disclosure, a cosmetic composition comprising a fermented grape extract obtained by fermenting grape (*Vitis vinifera*) berries using fungus of the genus *Botrytis* is disclosed.

10 Claims, 11 Drawing Sheets

COSMETIC COMPOSITION COMPRISING FERMENTED GRAPE EXTRACT

TECHNICAL FIELD

The present disclosure relates to a method for preparing a fermented grape extract and a cosmetic composition using the same, and more specifically, to an extraction method for fermenting and extracting grape berries and a cosmetic composition using the same.

BACKGROUND ART

As there is growing interest in products comprising natural components that minimize chemical components harmful to skin and use natural materials, research on cosmetics containing natural extracts has also been actively conducted. A natural extract may be an extract extracted from natural materials such as plants or fruits, and refers to an extract containing plant components in a broad sense.

Natural extracts contained in cosmetics are mostly extracted from fruits or plants, and various extracts having skin-improving effects such as skin protection, soothing, whitening, and moisturizing have been developed. In particular, a grape extract, which is extracted from grapes, is a natural extract that is known to be suitable for skin care cosmetics because the grape extract is effective for preventing skin aging, improving skin resistance, and soothing skin.

Therefore, there is a need in the art for a method for extracting a fermented grape extract, which exhibits a better anti-aging effect for skin than common grape extracts, and a cosmetic composition using a fermented grape extract.

Korean Patent No. 10-1778538 and the like have been published as related art documents of the present disclosure.

DISCLOSURE

Technical Problem

The present disclosure has been made in an effort to solve the problems in the related art, and to provide a method for extracting a fermented grape extract and a cosmetic composition using a fermented grape extract.

The technical problems of the present disclosure are not limited to the aforementioned technical problems, and other technical problems, which have not been mentioned, may be clearly understood by a person with ordinary skill in the art from the following description.

Technical Solution

According to an exemplary embodiment of the present disclosure for solving the problems as described above, a cosmetic composition comprising a fermented grape extract obtained by fermenting grape (*Vitis vinifera*) berries using a fungus of the genus *Botrytis* is disclosed.

Alternatively, the fungus of the genus *Botrytis* is a noble rot (Edelfaule) fungus, and may comprise *Botrytis cinerea*.

Alternatively, the cosmetic composition may be comprising 0.001% or more and 10% or less of the fermented grape extract with respect to the cosmetic composition.

Alternatively, the cosmetic composition may be characterized as a formulation for use on skin of a user.

Alternatively, the cosmetic composition may be characterized by having anti-aging effect for skin compared to a common unfermented grape extract.

Alternatively, the cosmetic composition may further comprise at least one of an additive or a polyol, and the additive may comprise at least one of a thickener or a preservative.

According to another exemplary embodiment of the present disclosure for solving the problems as described above, a method for preparing a fermented grape extract for a cosmetic composition is disclosed. The method may comprise crushing sterilized grape berries, placing the grape berries on a solid medium, inoculating the grape berries with a fungus of the genus *Botrytis*, and fermenting the grape berries during a fermentation period.

Alternatively, the fermentation period may be 10 days or more and 20 days or less.

Alternatively, the method may further comprise ultrasonically extracting the fermented grape berries using 50% or more and 99% or less ethanol (EtOH).

Alternatively, a ratio of the fermented grape berries and the ethanol may be 1:10.

The technical solutions which can be obtained from the present disclosure are not limited to the solutions mentioned above, and other solutions which have not been mentioned will be apparently understood by a person of ordinary skill in the art to which the present disclosure pertains from the following description.

Advantageous Effects

According to exemplary embodiments of the present disclosure, it is possible to provide a fermented grape extract having excellent anti-aging effects for skin compared to a common grape extract, and a method for preparing a fermented grape extract.

The technical effects which can be obtained from the present disclosure are not limited to the effects mentioned above, and other effects which have not been mentioned will be apparently understood by a person of ordinary skill in the art to which the present disclosure pertains from the following description.

BEST MODE

Figure 1:
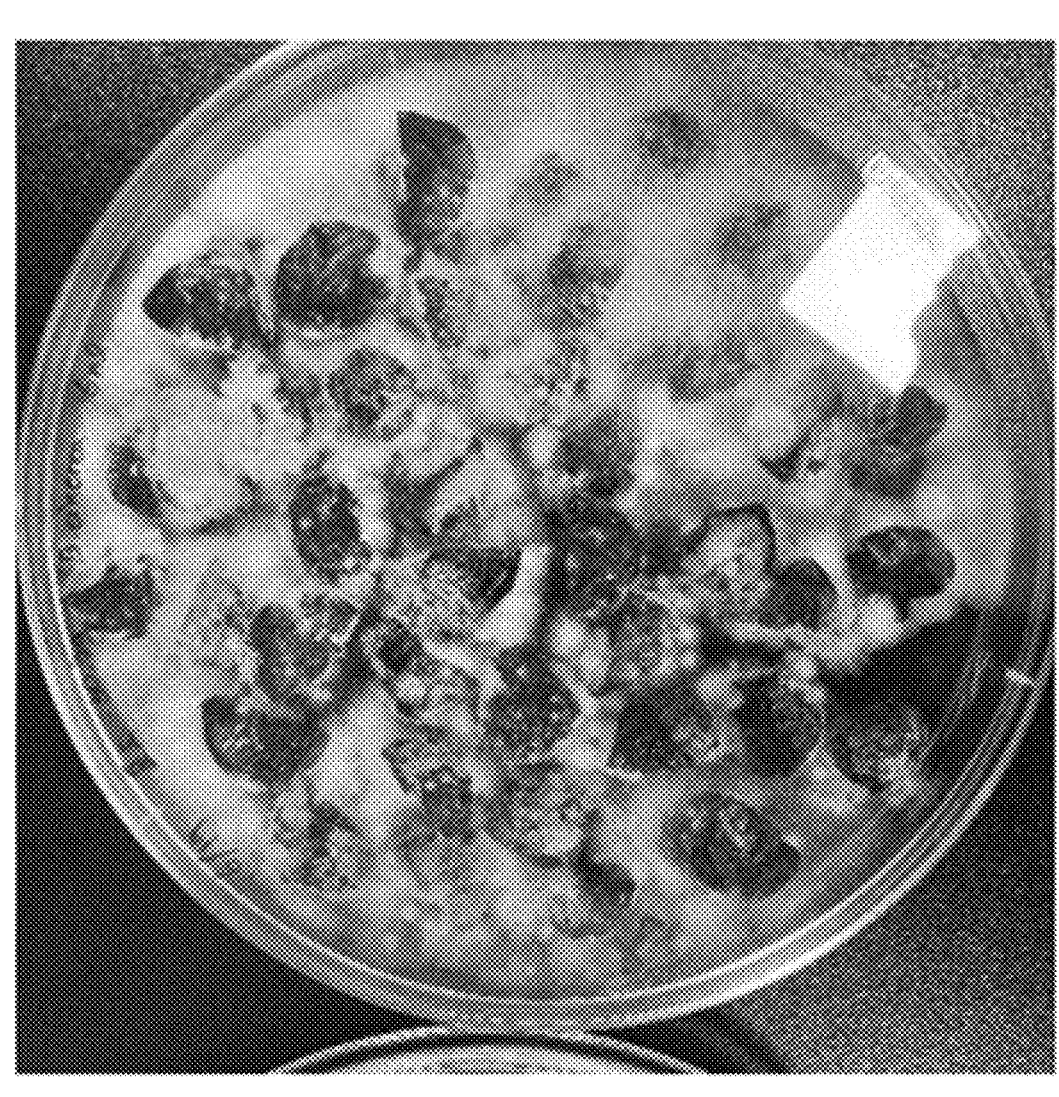
FIG. 1 is a photograph taken of grape berries fermented by *Botrytis cinerea*, according to an exemplary embodiment of the present disclosure.

Various exemplary embodiments will be now described with reference to the drawings. In the present specification, various descriptions are presented to provide an understanding of the present disclosure. However, it is apparent that these exemplary embodiments may be practiced without such specific description.

In addition, the term "or" is intended to mean an inclusive "or" rather than an exclusive "or." That is, it is intended to mean one of the natural inclusive substitutions of "X uses A or B" unless otherwise specified or clear from the context. That is, when X uses A; X uses B; or X uses both A and B, then "X uses A or B" can be applied to any of these cases. Furthermore, as used herein, the term "and/or" should be understood to refer to and comprise all possible combinations of one or more of the listed related items.

Further, the terms "comprise" and/or "comprising" should be understood to mean that the corresponding feature and/or element is present. However, the terms "comprise" and/or "comprising" should be understood as not excluding the presence or addition of one or more different features, components and/or groups thereof. In addition, unless otherwise specified or when the context is not clear as indicating a singular form, the singular in the present specification and claims should be interpreted as meaning "one or more" in general.

A cosmetic composition of the present disclosure may be a composition which may be comprised of functional products for improving skin, such as pharmaceuticals, external preparations and cosmetics. Examples of a product which may comprise a cosmetic composition of the present disclosure comprise a basic cosmetic (for example, toner, ampoule, essence, lotion, cream, and the like), a cleansing product (for example, shampoo, conditioner, soap, cleansing foam, body cleanser, and the like). The above-described products are only examples, and the examples described above should not be construed as limiting products which may comprise a cosmetic compositions of the present disclosure.

Skin improvement of the present disclosure may mean that skin has been improved for cosmetic or medical purposes such as skin wrinkle amelioration, anti-inflammatory effect, antioxidant effect, skin elasticity increase, skin moisturizing, skin barrier strengthening and whitening.

Anti-aging effect for skin of the present disclosure means effect of preventing skin aging, and may comprise specifically skin wrinkle-ameliorating effect, anti-inflammatory effect and antioxidant effect.

Skin aging of the present disclosure may mean intrinsic aging due to age and genetic factors. Furthermore, Skin aging of the present disclosure may also mean photo-aging due to external environmental factors such as light comprising sunlight, wind and coldness.

A cosmetic composition according to exemplary embodiments of the present disclosure may comprise other cosmetic compositions and other components that can be blended as described below. Specifically, a cosmetic composition of the present disclosure may comprise 0.001% or more and 10% or less of a fermented grape extract, 40% or more and 70% or less of a polyol, and 1% or more and 10% or less of an additive with respect to a cosmetic composition.

Specifically, the polyol of the present disclosure may comprise at least one of glycerin, 1,3-butylene glycol, 1,3-propanediol, methylepropanediol, propylene glycol, dipropylee glycol, phentylene glycol, 1,2-hexanediol.

To enhance usefulness such as stability and quality of a cosmetic composition of the present disclosure, the cosmetic composition may further comprise acceptable additives additionally. Such additives may comprise a stabilizer, a solubilizer, an emulsifier, a vitamin, a pigment, a fragrance, a carrier, a chelating agent, an antioxidant, a bactericide, a thickener, a preservative, or a combination thereof, and the like, and may vary depending on the type of formulation to be prepared.

The thickener which may be comprised of additives of the present disclosure is for increasing a viscosity of a cosmetic composition, and may comprise at least one of xanthan gum, a carrageenan powder, a carbomer, a sodium carbomer or an acrylate polymer. The above-described thickener components are only examples, and the examples described above should not be construed as limiting components which may be comprised of the thickener of the present disclosure.

In addition, the preservative which may be comprised of the additive of the present disclosure can prevent spoilage due to chemical changes in a cosmetic composition, and may comprise at least one of ethylhexylglycerin or phenoxy ethanol. The above-described preservative components are only examples, and the examples described above should not be construed as limiting components which may be comprised of the preservative of the present disclosure.

A cosmetic composition of the present disclosure may be manufactured into a formulation for use on skin of a user by a method widely known in the cosmetic field. That is, the cosmetic composition according to exemplary embodiments of the present disclosure may be prepared in any formulation typically prepared in the art. Examples of any formulation comprise a solution, a suspension, an emulsion, a paste, a gel, a cream, a lotion, a shampoo, a surfactant-containing cleanser, a softening lotion, a nourishing lotion, a nourishing emulsion, a massage cream, an essence, an eye cream, a cleansing cream, a cleansing foam, a cleansing water, a pack, and the like.

Other components that can be blended into a cosmetic composition according to exemplary embodiments of the present disclosure comprise oil and fat components, emollients, organic and inorganic pigments, organic powders, ultraviolet absorbers, pH adjusters, alcohols, pigments, fragrances, and blood flow stimulants, cooling agents, anhydrotics, and the like.

A cosmetic composition of the present disclosure may be applied by being applied in an appropriate amount according to skin site and area to be applied, and may be used repeatedly once to several times a day, if necessary. Further, the amount and frequency of application may be increased or decreased, if necessary, according to skin condition, age and the like of an individual.

A cosmetic composition of the present disclosure may be a composition comprising two or more essential components for a main effect among the components comprised of the cosmetic composition. The main effect is an effect that appears after applying the cosmetic composition to skin, and may be a whitening effect, a wrinkle-ameliorating effect, but the present disclosure is not limited thereto.

A fungus of the genus *Botrytis* of the present disclosure may mean a fungus classified into the genus *Botrytis* which can cause noble rot (Edelfaule) in fruits and vegetables. The fungus of the genus *Botrytis* of the present disclosure comprises *Botrytis cinerea*, also known as gray filamentous fungus or *Botrytis cinerea*.

A fermented grape extract of the present disclosure may mean an extract for a cosmetic composition extracted using grape berries fermented by *Botrytis cinerea* according to an exemplary embodiment of the present disclosure.

Grape berries of a fermented grape extract of the present disclosure is a fruit of *Vitis vinifera* plant, and may comprise at least one of husks, seeds and pulps of grape berries.

A common grape extract of the present disclosure may mean an extract extracted using unfermented grape berries.

Hereinafter, a method for preparing a fermented grape extract obtained by fermenting grape (*Vitis vinifera*) berries using *Botrytis cinerea* among a fungus of the genus *Botrytis* will be described.

Example 1. Preparation of Fermented Grape Extract

Example 1, which is a fermented grape extract, was prepared as follows according to a method for preparing a fermented grape extract according to a preferred exemplary embodiment of the present disclosure.

According to a preferred exemplary embodiment of the present disclosure, a method for preparing a fermented grape extract comprises steps of 1) culturing *Botrytis cinerea,* 2) fermenting one or more grape berries using the cultured *Botrytis cinerea*, and 3) extracting an extract from the fermented grape berries.

Hereinafter, the steps of 1) culturing *Botrytis cinerea* for fermentation of grape berries will be specifically described.

A potato dextrose agar (PDA) medium was prepared for culturing *Botrytis cinerea* of the present disclosure, inoculated with *Botrytis cinerea* and cultured for 7 to 14 days. In addition, for subculture, a medium in which *Botrytis cinerea* had been cultured was cut and transplanted to center of a newly prepared PDA medium.

Thereafter, 10 ml of a 0.02% glycerol (in DW) solution was added to the PDA medium in which *Botrytis cinerea* had been cultured, and a platinum loop was used to obtain *Botrytis cinerea* hyphae and spores. A suspension of noble rot spores obtained was used after being filtered using a syringe inserted with a sterilized absorbent cotton having a thickness of about 0.5 cm to 1 cm.

Hereinafter, the steps of 2) fermenting one or more grape berries using cultured *Botrytis cinerea* will be described in detail.

Grape berries used in the present disclosure were washed in running water, dried, stored, autoclaved at 121° C. for 15 minutes prior to fermentation, and then crushed to ½ to ¼ of the current grape berry size under aseptic conditions.

Sterilized crushed grape berries were put on a new potato dextrose agar (PDA) medium, and the grape berries were inoculated with *Botrytis cinerea* by sprinkling noble rot sporesuspensions (2 to $5*10^4$) on the grape berries. The grape berries inoculated with *Botrytis cinerea* were subjected to solid state fermentation at 25° C. for 10 days to 20 days.

The appearance of grape berries fermented according to the steps described above is illustrated in FIG. 1. FIG. 1 is a photograph taken of grape berries fermented by *Botrytis cinerea*, according to an exemplary embodiment of the present disclosure.

Hereinafter, the steps of 3) extracting an extract from the fermented grape berries will be described in detail.

Fully fermented grape berries were harvested and sterilized at 121° C. for 15 minutes. The sterilized fermented grape berries were mixed with 70% ethanol (EtOH) as an extraction solvent at a weight ratio of 1:10, and a primary extract was extracted through ultrasonic extraction. Specifically, ultrasonic extraction was performed at 60° C. for 90 minutes, and a ultrasonically extracted primary extract was filtered using filter paper and a extraction solvent was removed using a vacuum evaporator, and finally the fermented grape extract of Example 1 was obtained.

Comparative Example 1. Preparation of Grape Extract

In order to compare effects of Example 1 described above, Comparative Example 1, which is a common grape extract, was prepared as follows.

Unlike Example 1, Comparative Example 1 was prepared through the steps of extracting an extract from grape berries, except for the steps of fermenting grape berries. That is, Comparative Example 1 was extracted by the same as the steps of 3) extracting an extract from the fermented grape berries in Example 1 using unfermented grape berries. Specifically, the steps of preparing Comparative Example 1 are as follows.

Grape berries were mixed with 70% ethanol (EtOH) as an extraction solvent at a weight ratio of 1:10, and a primary extract was extracted through ultrasonic extraction at 60° C. for 90 minutes. The ultrasonically extracted primary extract was filtered using filter paper, and the extraction solvent was removed using a vacuum concentrator, and finally the grape extract of Comparative Example 1 was obtained.

Hereinafter, Experimental Examples 1 to 5, in which skin wrinkle-ameliorating effect, anti-inflammatory effect and antioxidant effect of each of Example 1 and Comparative Example 1 prepared were comparatively evaluated will be described below.

Deficiency of collagen and structural deformation of elastin have been suggested as causes of skin wrinkles in regard to skin aging. Collagen and elastin are major proteins that make up the dermis of skin and serve to maintain the structure and elasticity of skin. Accordingly, the more collagen and elastin are produced, the elasticity of skin increases and the wrinkles are ameliorated, thereby preventing skin aging.

In order to evaluate skin wrinkle-ameliorating effects of Example 1 and Comparative Example 1 as described above, Experimental Examples 1 to 3 related to collagen production and elastin production, which are highly related to skin wrinkles, were performed as follows.

Experimental Example 1. Evaluation of Changes in Collagen/Collagenase Gene Expression Collagenase is an enzyme that degrades collagen, and the more collagenase is produced, the collagen is reduced, which reduces skin elasticity and increases wrinkles, thereby accelerating skin aging.

Accordingly, in order to evaluate skin wrinkle-ameliorating effects of Example 1 and Comparative Example 1, Experimental Example 1 was performed, in which changes in collagen/collagenase gene expression were measured.

Figure 2A:
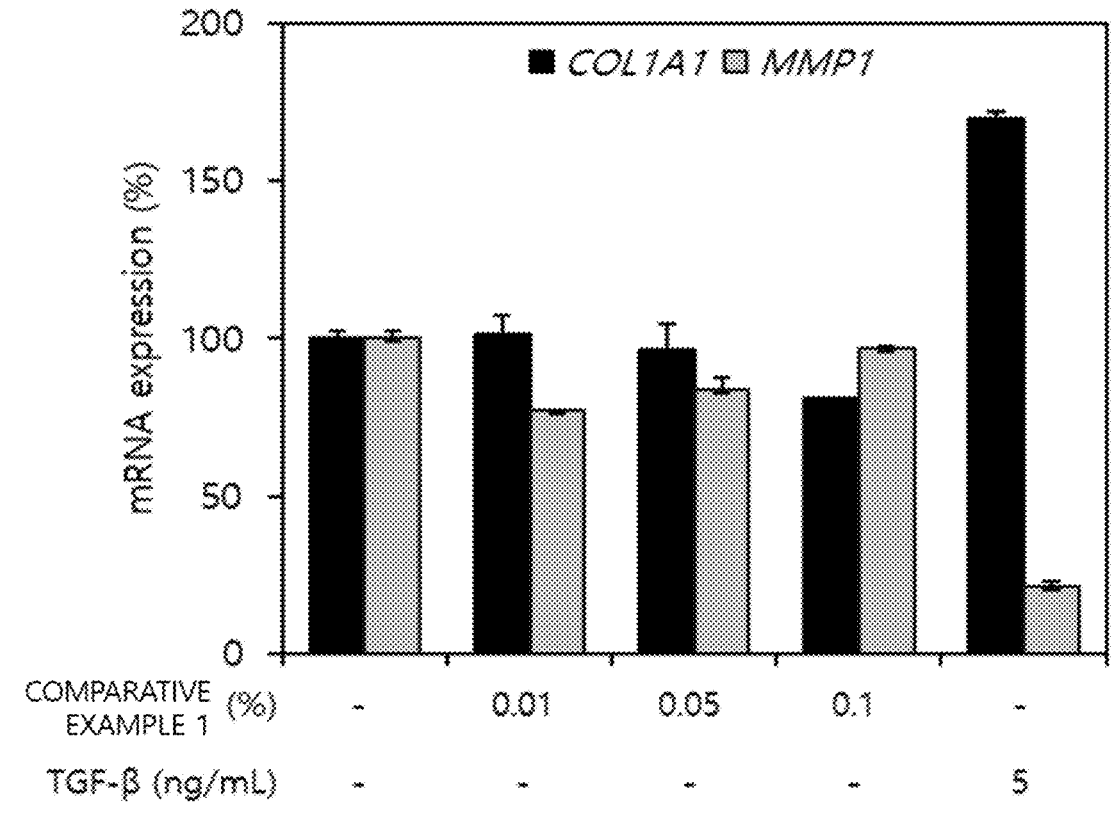
FIG. 2A is a graph showing mRNA expression levels (%) of collagen gene (COL1A1) and collagenase gene (MMP1) according to concentrations (%) of Comparative Example 1 of the present disclosure.
Figure 2B:
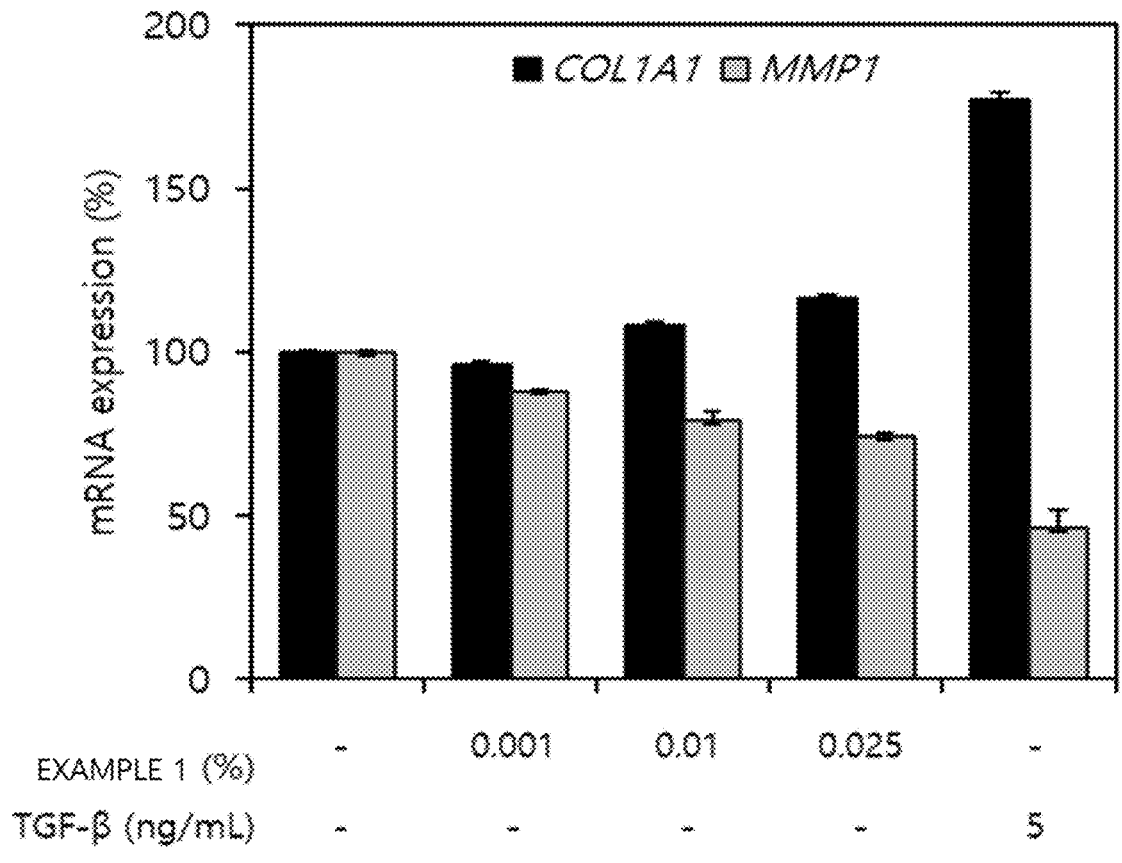
FIG. 2B is a graph showing mRNA expression levels (%) of collagen gene (COL1A1) and collagenase gene (MMP1) according to concentrations (%) of Example 1 of the present disclosure.

Specifically, mRNA expression levels (%) of collagen gene (COL1A1) and collagenase gene (MMP1) were measured according to concentrations (%) of Example 1 and Comparative Example 1, and results are shown in FIGS. 2A and 2B.

FIG. 2A is a graph showing mRNA expression levels (%) of collagen gene (COL1A1) and collagenase gene (MMP1) according to concentrations (%) of Comparative Example 1 of the present disclosure. Specifically, horizontal axis (x-axis) in FIG. 2A indicates the concentrations (%) of Comparative Example 1, and vertical axis (y-axis) indicates mRNA expression levels (%).

As illustrated in FIG. 2A, referring to a graph of the COL1A1 mRNA expression levels (%) according to the concentrations (%) of Comparative Example 1, it can be observed that the COL1A1 mRNA expression level (%) of Comparative Example 1 at a concentration of 0.1% is lower than the COL1A1 mRNA expression level (%) of Comparative Example 1 at a concentration of 0.01%. Further, as illustrated in FIG. 2A, it can be observed that the MMP1 mRNA expression level (%) of Comparative Example 1 at a concentration of 0.1% is higher than the MMP1 mRNA expression level (%) of Comparative Example 1 at a concentration of 0.01%.

Therefore, it can be seen that the higher concentration (%) of Comparative Example 1, the lower collagen gene mRNA expression level (%) and the higher the collagenase gene mRNA expression level (%).

FIG. 2B is a graph showing mRNA expression levels (%) of collagen gene (COL1A1) and collagenase gene (MMP1) according to concentrations (%) of Example 1 of the present disclosure. Specifically, horizontal axis (x-axis) in FIG. 2B indicates the concentrations (%) of Example 1, and vertical axis (y-axis) indicates the mRNA expression levels (%).

As illustrated in FIG. 2B, referring to a graph of the COL1A1 mRNA expression levels (%) according to the concentrations (%) of Example 1, it can be observed that the COL1A1 mRNA expression level (%) of Example 1 at a concentration of 0.001% is higher than the COL1A1 mRNA expression level (%) of Example 1 at a concentration of 0.025%. In addition, as illustrated in FIG. 2B, it can be observed that the MMP1 mRNA expression level (%) of Example 1 at a concentration of 0.001% is lower than the MMP1 mRNA expression level (%) of Example 1 at a concentration of 0.025%.

Therefore, it can be seen that the higher concentration (%) of Example 1, the higher collagen gene mRNA expression level (%) and the lower collagenase gene mRNA expression level (%).

As described above with reference to FIGS. 2A and 2B, it can be seen that Example 1 is excellent in increasing collagen production and inhibiting collagenase production compared to Comparative Example 1.

Experimental Example 2. Evaluation of Elastin/Elastase Production

Elastase is an enzyme that degrades elastin, and it is known that increased activity of elastase distorts a three-dimensional structure of elastin and induces skin wrinkles.

Accordingly, in order to evaluate skin wrinkle-ameliorating effects of Example 1 and Comparative Example 1, Experimental Example 2 was performed, in which elastin/elastase mRNA expression levels (%) were measured. Specifically, mRNA expression levels (%) of elastin (ELN) and elastase (MMP12) were measured according to concentrations (%) of Example 1 and Comparative Example 1, and the results are shown in FIGS. 3A and 3B.

Figure 3A:
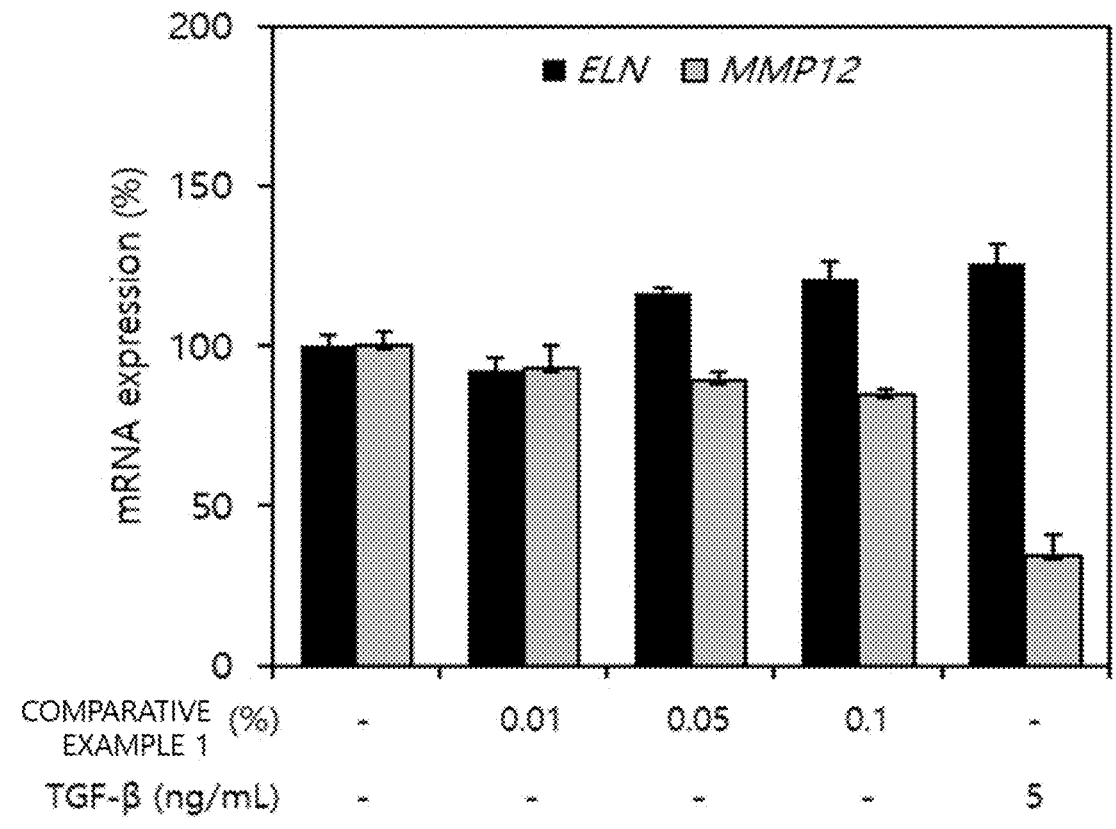
FIG. 3A is a graph showing mRNA expression levels (%) of elastin (ELN) and elastase (MMP12) according to concentrations (%) of Comparative Example 1 of the present disclosure.

FIG. 3A is a graph showing mRNA expression levels (%) of elastin (ELN) and elastase (MMP12) according to concentrations (%) of Comparative Example 1 of the present disclosure. Specifically, horizontal axis (x-axis) in FIG. 3A indicates the concentrations (%) of Comparative Example 1, and vertical axis (y-axis) indicates the mRNA expression levels (%).

Figure 3B:
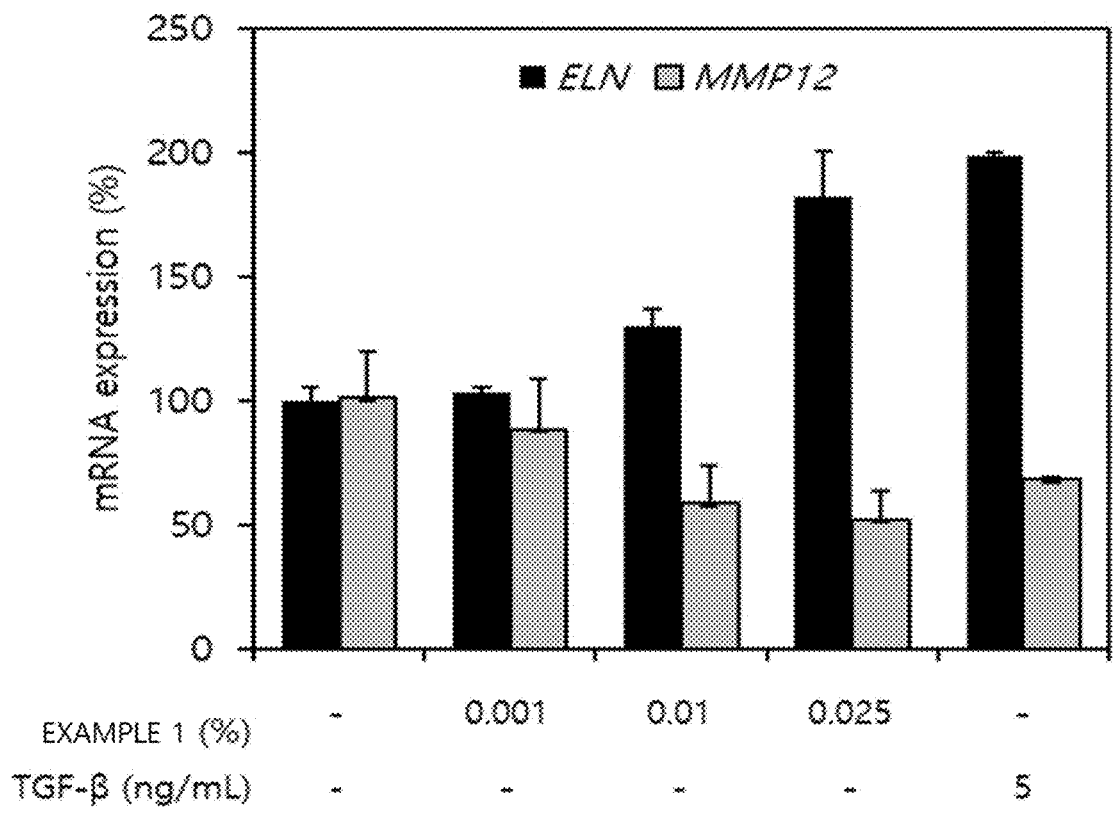
FIG. 3B is a graph showing mRNA expression levels (%) of elastin (ELN) and elastase (MMP12) according to concentrations (%) of Example 1 of the present disclosure.

FIG. 3B is a graph showing mRNA expression levels (%) of elastin (ELN) and elastase (MMP12) according to the concentration (%) of Example 1 of the present disclosure. Specifically, horizontal axis (x-axis) in FIG. 3B indicates the concentrations (%) of Example 1, and vertical axis (y-axis) indicates the mRNA expression levels (%).

As shown in FIGS. 3A and 3B, both Comparative Example 1 and Example 1 showed a tendency that as the concentrations (%) increased, the elastin (ELN) mRNA expression levels (%) increased, and the elastase (MMP12) mRNA expression levels (%) decreased.

However, as shown in FIGS. 3A and 3B, it can be seen that the amount of increase in elastin (ELN) mRNA expression level (%) according to the concentration (%) in Example 1 is much higher than the amount of increase in elastin (ELN) mRNA expression levels (%) according to the concentrations (%) in Comparative Example 1.

That is, as shown in FIG. 3A, it can be seen that as the elastin (ELN) mRNA expression levels (%) in Comparative Example 1 shows a tendency to gradually increase according to the concentrations (%), there is no significant difference in the elastin (ELN) mRNA expression levels (%).

In contrast, as shown in FIG. 3B, it can be seen that as the elastin (ELN) mRNA expression levels (%) in Example 1 rapidly increases according to the concentrations (%), the elastin (ELN) mRNA expression levels (%) in Example 1 whose concentration of 0.025% is close to 200%.

Furthermore, as shown in FIG. 3A, the elastase (MMP12) mRNA expression levels (%) in Comparative Example 1 shows a tendency to gradually decrease according to the concentrations (%), and in contrast, as shown in FIG. 3B, the elastase (MMP12) mRNA expression levels (%) in Example 1 shows a tendency to rapidly decrease according to concentrations (%).

As described above with reference to FIGS. 3A and 3B, it can be seen that Example 1 is excellent in effects of increasing elastin production and inhibiting elastase production compared to Comparative Example 1.

Experimental Example 3. Evaluation of Elastase Activity Inhibition

As described above, when an activity of elastase is increased, skin elasticity is decreased, which may be a major cause of wrinkle formation. Accordingly, a inhibition of elastase activity can be seen as an important issue in improving skin elasticity and ameliorating wrinkles.

Figure 4A:
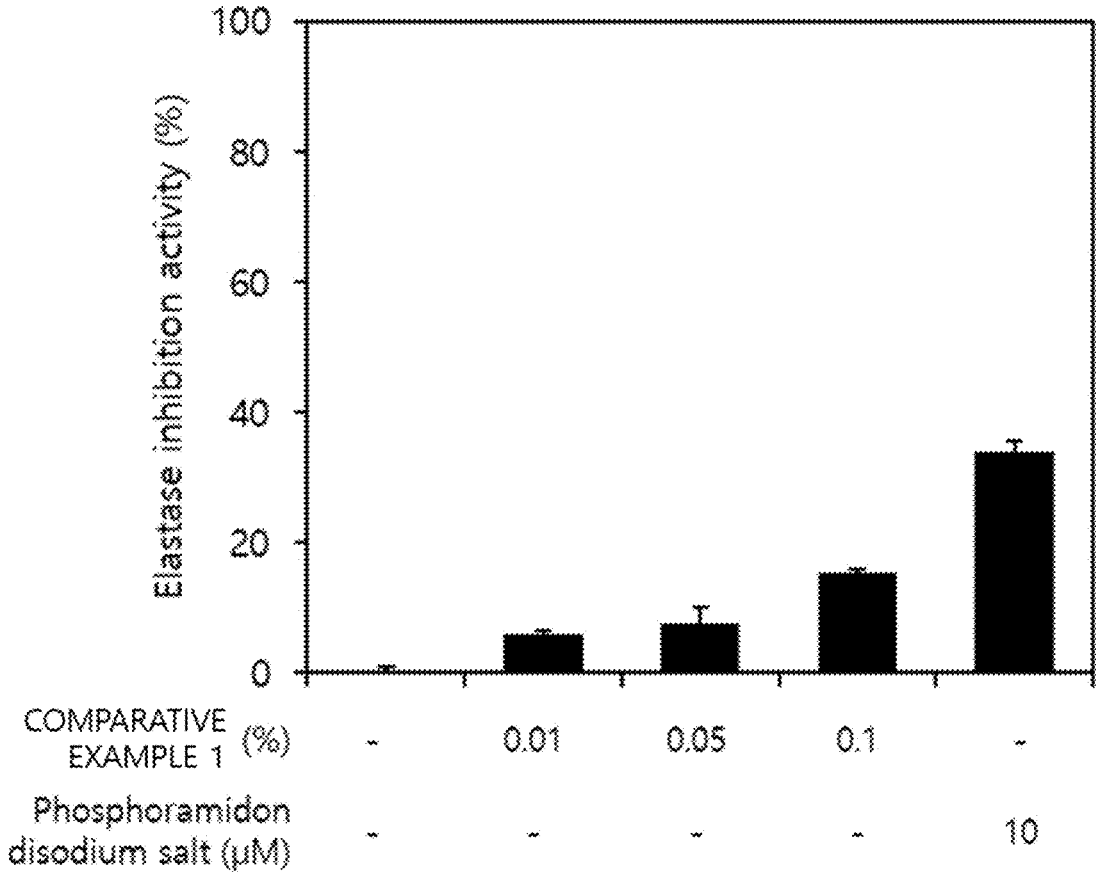
FIG. 4A is a graph showing the amount of elastase inhibition activity (%) according to concentrations (%) of Comparative Example 1 of the present disclosure.
Figure 4B:
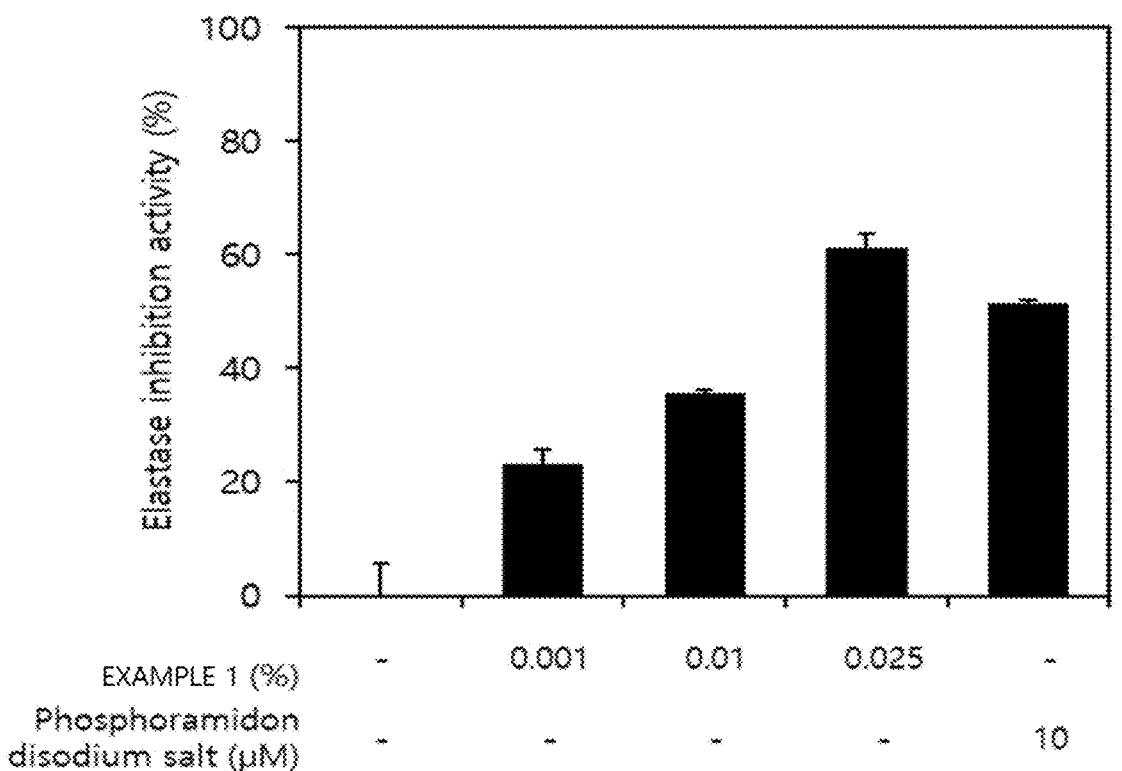
FIG. 4B is a graph showing the amount of elastase inhibition activity (%) according to concentrations (%) of Example 1 of the present disclosure.

Accordingly, in the present Experimental Example 3, the amount of elastase inhibition activities (%) according to concentrations (%) of each of Comparative Example 1 and Example 1 was measured, and results are shown in FIGS. 4A and 4B.

FIG. 4A is a graph showing the amount of elastase inhibition activities (%) according to concentrations (%) of Comparative Example 1 of the present disclosure. Specifically, the horizontal axis (x-axis) in FIG. 4A indicates the concentrations (%) of Comparative Example 1, and vertical axis (y-axis) indicates the amount of elastase inhibition activities (%).

FIG. 4B is a graph showing the amount of elastase inhibition activities (%) according to concentrations (%) of Example 1 of the present disclosure. Specifically, horizontal axis (x-axis) in FIG. 4B indicates concentrations (%) of Example 1, and vertical axis (y-axis) indicates the amount of elastase inhibition activities (%).

As shown in FIGS. 4A and 4B, it can be seen that the amount of elastase inhibition activities (%) of Example 1 shown in FIG. 4B is much higher than the amount of elastase inhibition activities (%) of Comparative Example 1 shown in FIG. 4A.

Specifically, as shown in FIGS. 4A and 4B, it can be seen that when comparing elastase inhibition activities (%) of Example 1 and Comparative Example 1 at the same concentration of 0.01%, the amount of elastase inhibition activity of Example 1 is much higher than that of Comparative Example 1.

In addition, it can be seen that the amount of elastase inhibition activity (%) of Comparative Example 1 with the highest concentration of 0.1% illustrated in FIG. 4A is remarkably lower than the amount of elastase inhibition activity (%) of Example 1 with a concentration of 0.025% illustrated in FIG. 4B.

As described above with reference to FIGS. 4A and 4B, it can be seen that Example 1 is excellent in effects of inhibiting elastase compared to Comparative Example 1.

As described above, through the above-described Experimental Examples 1 to 3, it can be seen that Example 1 is excellent in effects of promoting production of collagen and elastin, which can prevent formation of skin wrinkles, compared to Comparative Example 1, and is also excellent in effects of suppressing the formation of collagenase and elastase, which may promote skin aging.

That is, it can be seen that the fermented grape extract extracted from fermented grape berries has excellent effects in increasing skin elasticity and ameliorating skin wrinkles compared to a common grape extract extracted from unfermented grape berries.

Experimental Example 4. Evaluation of Suppression of Intracellular Pro-Inflammatory Factors Skin inflammation is known to be a major cause of not only skin aging but also damage to healthy skin, such as damage to skin barrier and keratinization.

Figure 5A:
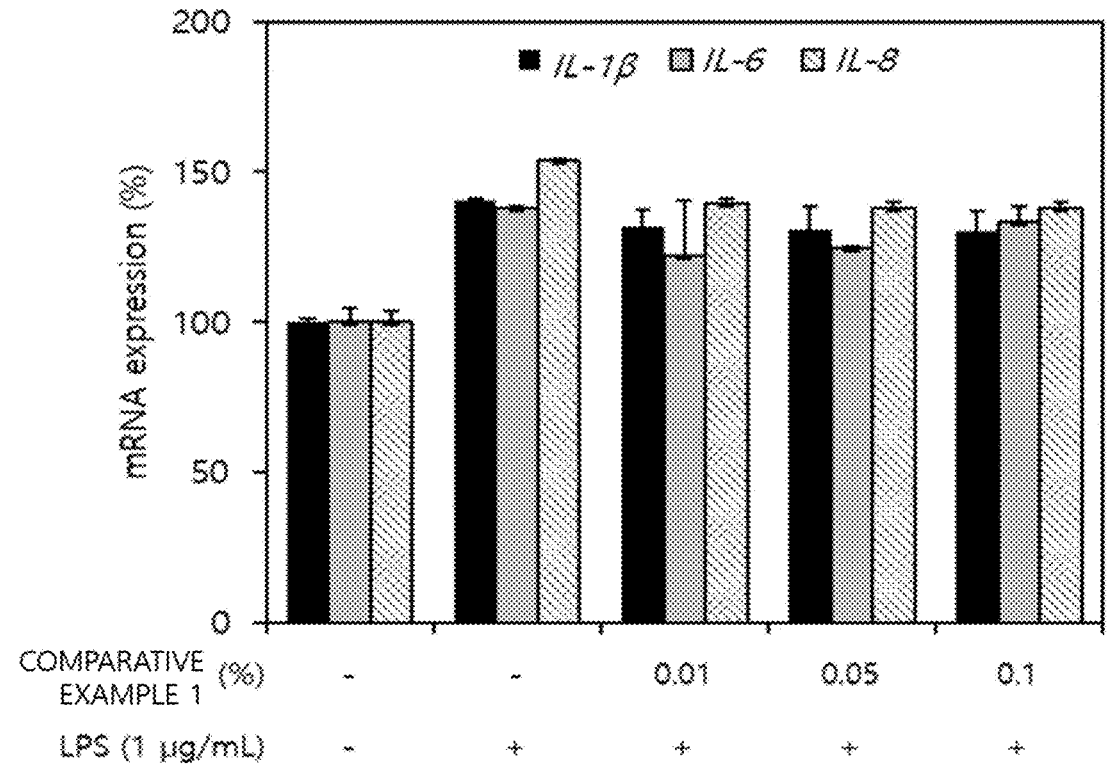
FIG. 5A is a graph showing mRNA expression levels (%) of each of IL-1β, IL-6 and IL-8 according to concentrations (%) of Comparative Example 1 of the present disclosure.
Figure 5B:
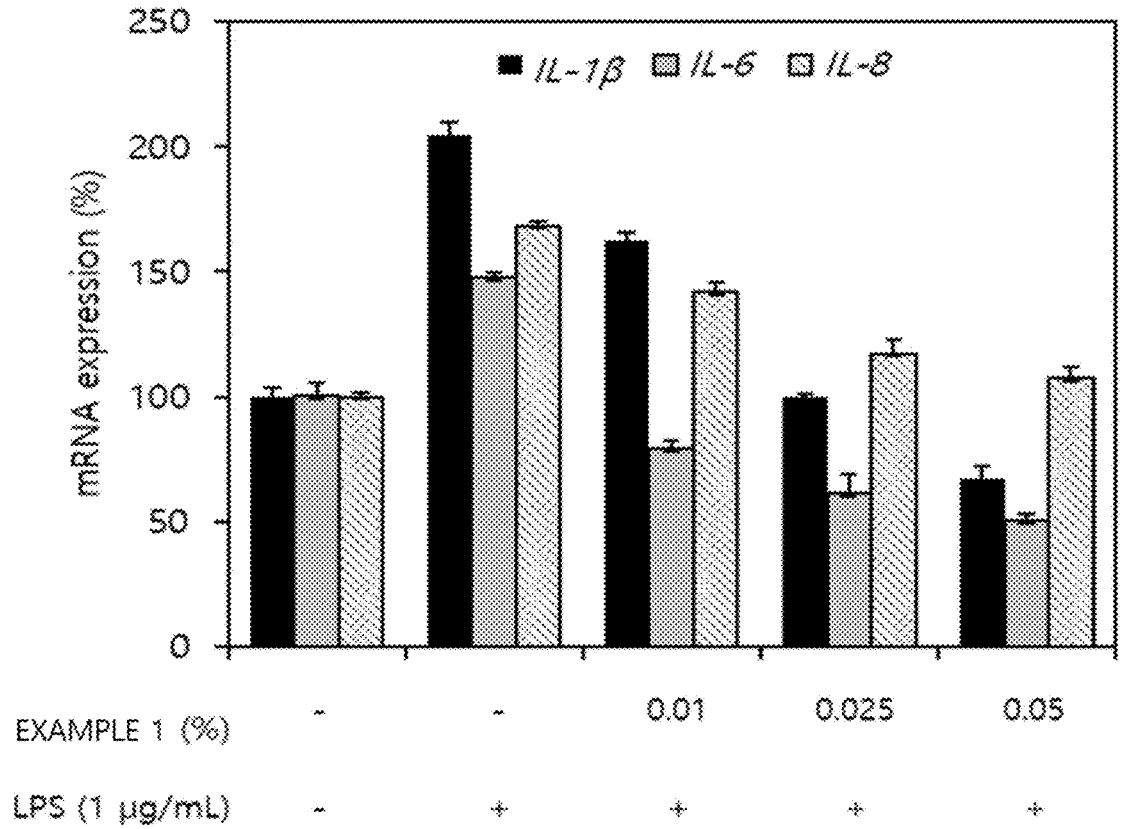
FIG. 5B is a graph showing mRNA expression levels (%) of each of IL-1β, IL-6 and IL-8 according to concentrations (%) of Example 1 of the present disclosure.

In order to evaluate an anti-inflammatory effect according to the concentrations (%) of each of Example 1 and Comparative Example 1, Experimental Example 4 for measuring mRNA expression levels (%) of each of the pro-inflammatory genes IL-1β, IL-6 and IL-8 was performed, and results are shown in FIGS. 5A and 5B.

FIG. 5A is a graph showing mRNA expression levels (%) of each of IL-1β, IL-6 and IL-8 according to concentrations (%) of Comparative Example 1 of the present disclosure. Specifically, horizontal axis (x-axis) in FIG. 5A indicates the concentrations (%) of Comparative Example 1, and vertical axis (y-axis) indicates mRNA expression levels (%) of each of IL-1β, IL-6 and IL-8.

FIG. 5B is a graph showing mRNA expression levels (%) of each of IL-1β, IL-6 and IL-8 according to concentrations (%) of Example 1 of the present disclosure. Specifically, horizontal axis (x-axis) in FIG. 5B indicates the concentrations (%) of Example 1, and vertical axis (y-axis) indicates the mRNA expression levels (%) of each of IL-1β, IL-6 and IL-8.

The mRNA expression levels (%) of each of IL-1β, IL-6 and IL-8 in Comparative Example 1 illustrated in FIG. 5A do not show a significant difference according to the concentrations. In contrast, it can be seen that the mRNA expression levels (%) of each of IL-1β, IL-6 and IL-8 in Example 1 illustrated in FIG. 5B are significantly reduced according to the concentrations.

Further, when comparing FIGS. 5A and 5B, it can be seen that the mRNA expression level (%) of the pro-inflammatory genes in Example 1 are much lower than the mRNA expression level (%) of the pro-inflammatory genes in Comparative Example 1 at the same concentration of 0.01%.

As above described with reference to FIGS. 5A and 5B, it can be seen that Example 1 is excellent in effects of suppressing the pro-inflammatory genes (IL-1β, IL-6 and IL-8) compared to Comparative Example 1.

That is, it can be seen that Example 1, which is a fermented grape extract extracted from fermented grape berries, has an excellent skin anti-inflammatory effect compared to Comparative Example 1, which is a common grape extract.

Experimental Example 5. Antioxidant Efficacy Evaluation

General antioxidation means the suppression of oxidation, and can be regarded as a factor related to aging process of cells. That is, oxidation of cells means the senescence of cells, and antioxidation can be regarded as an action to suppress the senescence of cells. Accordingly, antioxidation can also be regarded as an important factor in anti-aging for skin composed of cells.

Figure 6A:
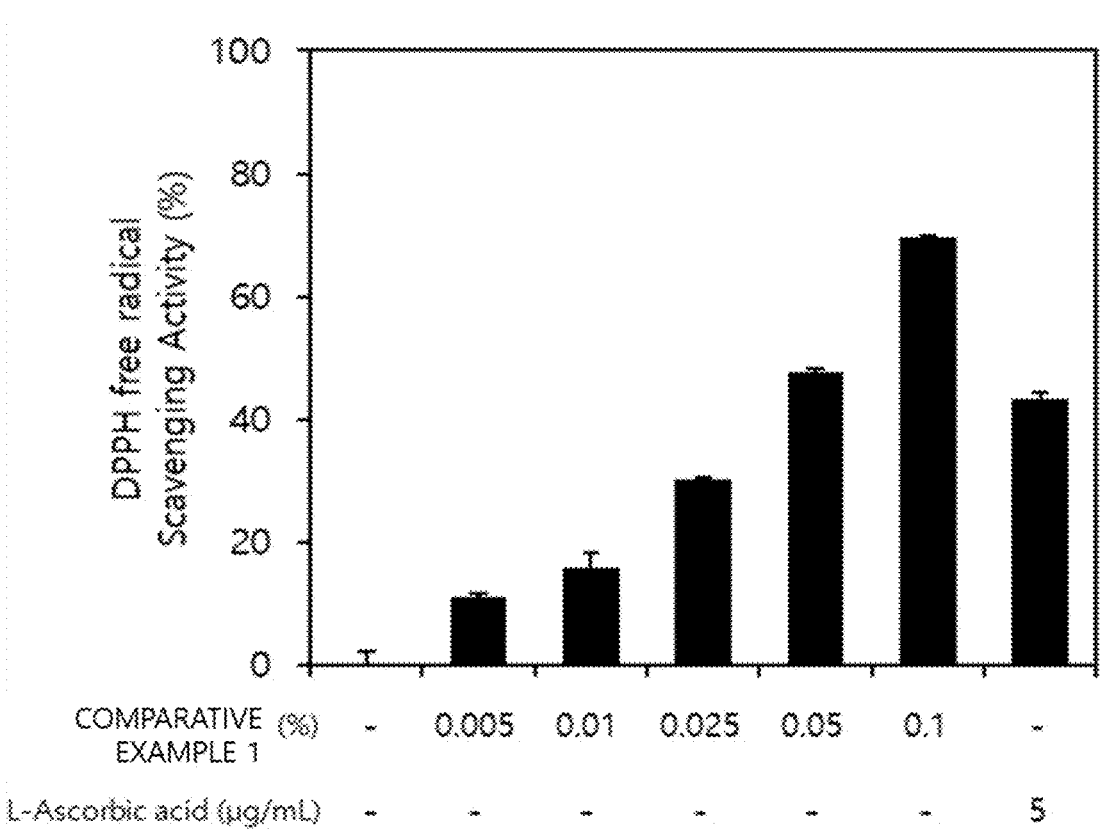
FIG. 6A is a graph showing DPPH free radical scavenging activity (%) according to concentrations (%) of Comparative Example 1 of the present disclosure.
Figure 6B:
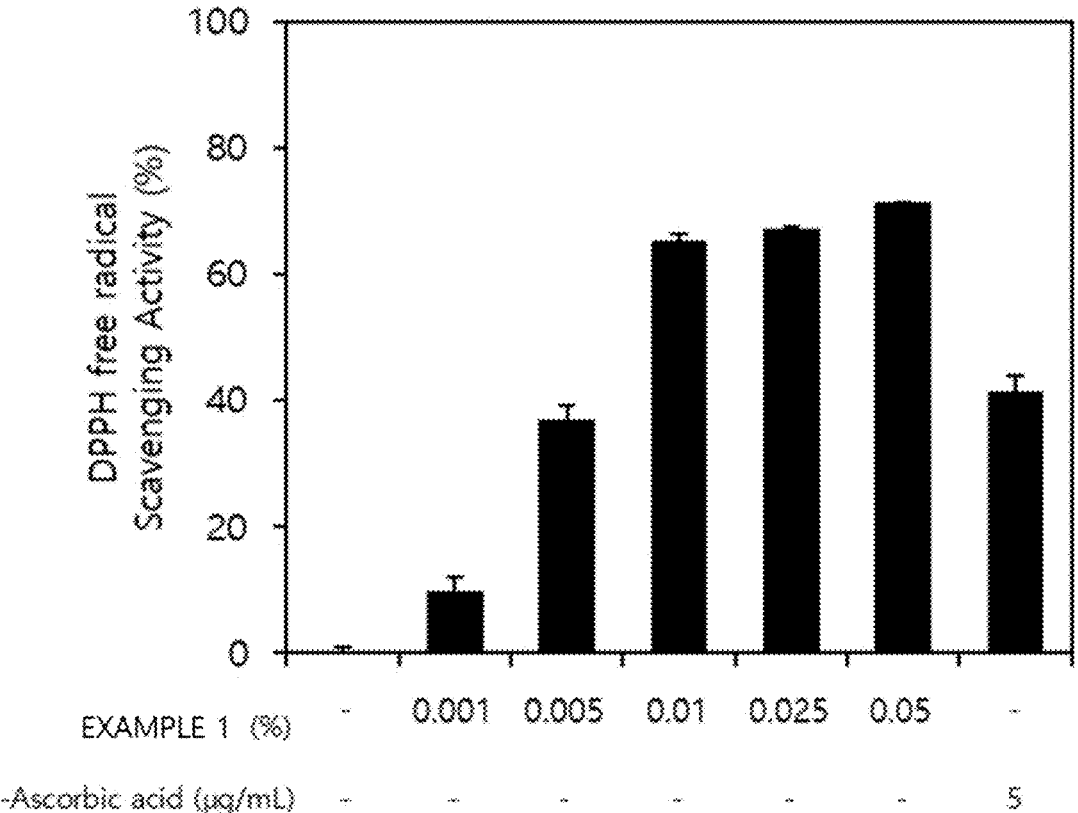
FIG. 6B is a graph showing DPPH free radical scavenging activity (%) according to concentrations (%) of Example 1 of the present disclosure.

Accordingly, Experimental Example 5 for measuring DPPH free radical scavenging activity using DPPH solution was performed in order to evaluate the antioxidant efficacy of each of Example 1 and Comparative Example 1, and results are shown in FIGS. 6A and 6B. In addition, L-ascorbic acid, which is a representative antioxidant, was used as a positive control in Experimental Example 5, which is an antioxidant measurement experiment.

FIG. 6A is a graph showing DPPH free radical scavenging activities (%) according to concentrations (%) of Comparative Example 1 of the present disclosure. Specifically, horizontal axis (x-axis) in FIG. 6A indicates concentrations (%) of Comparative Example 1, and vertical axis (y-axis) indicates the DPPH free radical scavenging activities (%).

FIG. 6A is a graph showing DPPH free radical scavenging activities (%) according to the concentrations (%) of Example 1 of the present disclosure. Specifically, horizontal axis (x-axis) in FIG. 6B indicates the concentrations (%) of Example 1, and vertical axis (y-axis) indicates the DPPH free radical scavenging activities (%).

In FIG. 6A, Comparative Example 1 shows a higher DPPH free radical scavenging activity (%) than a positive control L-ascorbic acid at a concentration of 0.05%. In contrast, in FIG. 6B, Example 1 shows much higher DPPH free radical scavenging activity (%) than a positive control at a concentration of 0.01%. Furthermore, according to FIGS. 6A and 6B, it can be seen that Example 1 has higher DPPH free radical scavenging activities (%) than Comparative Example 1 from a concentration of 0.005% or higher.

Accordingly, it can be seen that Example 1 can have an excellent antioxidant effect even at a lower concentration than Comparative Example 1.

That is, it can be seen that Example 1, which is a fermented grape extract extracted from fermented grape berries, has an excellent antioxidant effect compared to Comparative Example 1, which is a common grape extract.

Through the above-described Experimental Examples 1 to 3, it can be seen that a fermented grape extract prepared according to an exemplary embodiment of the present disclosure is effective in ameliorating skin wrinkles compared to a common grape extract, it can be seen through Experimental Example 4 that a fermented grape extract has an excellent anti-inflammatory effect, and it can be seen through Experimental Example 5 that a fermented grape extract has an excellent antioxidant effect.

As described above, according to an exemplary embodiment of the present disclosure, a remarkable effect of being able to provide a method for preparing a fermented grape extract having excellent anti-aging effects for skin even when the concentration is lower than that of a common grape extract, and a cosmetic composition comprising the fermented grape extract occurs.

The descriptions on the presented exemplary embodiments are provided to enable a person with ordinary skill in the art of the present disclosure to use or practice the present disclosure. Various modifications to such exemplary embodiments will be apparent to a person with ordinary skill in the art of the present disclosure. The general principles defined herein can be applied to other exemplary embodiments without departing from the scope of the present disclosure. Accordingly, the present disclosure is not limited to the exemplary embodiments presented herein. The present disclosure should be interpreted in the broadest scope consistent with the principles and novel features presented herein.

MODE FOR INVENTION

Related contents have been described in Best Mode for carrying Out the Invention as described above.

INDUSTRIAL APPLICABILITY

The present disclosure relates to a method for preparing a fermented grape extract and a cosmetic composition using the same, and more specifically, to an extraction method for fermenting and extracting grape berries and a cosmetic composition using the same.

The invention claimed is:

1. A cosmetic composition for increasing elastin production comprising a fermented grape extract obtained by crushing sterilized Vitis vinifera berries and fermenting the crushed *Vitis vinifera* berries using a fungus of genus *Botrytis* on a solid medium.

2. The cosmetic composition of claim 1, wherein the fungus of the genus *Botrytis* comprises *Botrytis cinerea*.

3. The cosmetic composition of claim 1, comprising 0.001% or more and 10% or less of the fermented grape extract with respect to the cosmetic composition.

4. The cosmetic composition of claim 1, wherein the cosmetic composition is characterized as a formulation for use on skin of a user.

5. The cosmetic composition of claim 1, wherein the cosmetic composition is characterized by having anti-aging effect for skin compared to a common unfermented grape extract.

6. The cosmetic composition of claim 1, wherein the cosmetic composition further comprises,
   at least one of an additive or a polyol, and
   wherein the additive comprises at least one of a thickener or a preservative.

7. A method for preparing a fermented grape extract for a cosmetic composition, wherein the method comprises:
   crushing sterilized grape berries, placing the grape berries on a solid medium, inoculating the grape berries with a fungus of the genus *Botrytis*, and
   fermenting the grape berries during a fermentation period.

8. The method of claim 7, wherein the fermentation period is 10 days or more and 20 days or less.

9. The method of claim 7, further comprising ultrasonically extracting the fermented grape berries using 50% or more and 99% or less ethanol.

10. The method of claim 9, wherein a ratio of the fermented grape berries and the ethanol is 1:10.

* * * * *